United States Patent [19]

Hidaka et al.

[11] Patent Number: 4,634,770
[45] Date of Patent: Jan. 6, 1987

[54] ISOQUINOLINESULFONAMIDE DERIVATIVES

[75] Inventors: Hiroyoshi Hidaka, c/o Medical Department, Mie University, 174, Edobashicho 2-chome, Tsu-shi, Mie-ken; Takanori Sone, Nobeoka, both of Japan

[73] Assignees: Asahi Kasei Kogyo Kabushiki Kaisha; Hiroyoshi Hidaka, both of Japan

[21] Appl. No.: 548,722

[22] Filed: Nov. 4, 1983

[30] Foreign Application Priority Data

Nov. 18, 1982 [JP] Japan ............................... 57-201085

[51] Int. Cl.⁴ .......................................... C07D 217/02
[52] U.S. Cl. .................................. 546/145; 544/333; 544/363; 544/402; 546/139; 546/148
[58] Field of Search ......................... 546/145; 514/307

[56] References Cited
U.S. PATENT DOCUMENTS 4,097,472 6/1978 Okamoto et al. ................... 546/145
4,097,591 6/1978 Okamoto et al. ................... 546/145

Primary Examiner—Richard L. Raymond
Assistant Examiner—James H. Turnipseed
Attorney, Agent, or Firm—Finnegan, Henderson, Farabow, Garrett, Dunner

[57] ABSTRACT

This invention relates to novel isoquinolinesulfonamide derivatives of Formula (I):

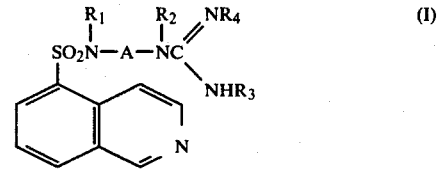

wherein A is a $C_{0-10}$ alkylene group or a $C_{0-10}$ alkylene group having a $C_{1-10}$ alkyl group, a phenyl group, a substituted phenyl group or a phenylalkyl group; $R_1$ and $R_2$ each is a hydrogen atom; or $R_1$ and $R_2$ are linked directly to form an ethylene group unsubstituted or substituted with a $C_{1-4}$ alkyl group;

$R_3$ and $R_4$ each is a hydrogen atom, a $C_{1-6}$ alkyl group or linked directly to form a $C_{2-6}$ alkylene group; and the pharmaceutically acceptable acid addition salt thereof, and to a process for preparing them. The isoquinoline derivatives possess a relaxatory action for vascular smooth muscle and action for increasing blood flow and are useful as a vasodilator and a hypotensor.

11 Claims, No Drawings

ISOQUINOLINESULFONAMIDE DERIVATIVES

BACKGROUND OF THE INVENTION

Field of the Invention

This invention relates to novel isoquinolinesulfonamide derivatives which possess a relaxatory action for vascular smooth muscle and action for increasing blood flow and are useful as a vasodilator and a hypotensor, and a process for the preparation thereof.

SUMMARY OF THE INVENTION

According to the present invention in one embodiment there is provided an isoquinoline derivative of Formula (I):

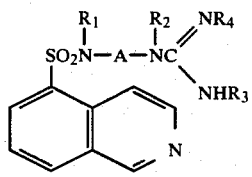

wherein A is a $C_{0-10}$ alkylene group or a $C_{0-10}$ alkylene group having a $C_{1-10}$ alkyl group, a phenyl group, a substituted phenyl group or a phenylalkyl group; $R_1$ and $R_2$ each is a hydrogen atom; or $R_1$ and $R_2$ are linked directly to form an ethylene group unsubstituted or substituted with a $C_{1-4}$ alkyl group;

$R_3$ and $R_4$ each is a hydrogen atom, a $C_{1-6}$ alkyl group or linked directly to form a $C_{2-6}$ alkylene group; and the pharmaceutically acceptable acid addition salt thereof.

The present invention in another embodiment provides a process of preparing the above described isoquinolinesulfonyl derivative.

DETAILED DESCRIPTION OF THE INVENTION

Exemplary A groups in Formula (I) include $C_{0-10}$ alkylene groups, preferably $C_{2-6}$ alkylene groups, such as ethylene, trimethylene, tetramethylene, pentamethylene, hexamethylene; and $C_{1-10}$ alkylene groups preferably $C_{2-6}$ alkylene groups, substituted by $C_{1-10}$ alkyl group such as methyl, ethyl, n-propyl, isopropyl, n-butyl, sec-butyl, isobutyl, n-pentyl, n-hexyl and n-octyl, a phenyl group, a substituted phenyl group or a phenylalkyl group such as benzyl and phenylethyl. In the compound of Formula (I), adjacent nitrogen atoms neighbor to A may be linked directly not through A. Direct linkage between the nitrogen atoms adjacent A in Formula I occurs when A is $C_0$ since there are then no carbon atoms between the nitrogen atoms adjacent A in Formula I. The $R_1$ and $R_2$ groups in Formula (I) each is a hydrogen atom; or $R_1$ and $R_2$ are linked directly to form an ethylene group. And 5- to 7-membered heterocyclic rings may be formed through an ethylene group and adjacent nitrogen atoms. Exemplary 5- to 7-membered heterocyclic rings include piperazine rings and homopiperazine rings. The ethylene groups formed by $R_1$ and $R_2$ may be substituted with a $C_{1-4}$ alkyl group. Exemplary substituents include methyl group, ethyl group, n-propyl group, isopropyl n-butyl group, isobutyl group, sec-butyl group. Exemplary $R_3$ and $R_4$ in Formula (I) include a hydrogen atom, a $C_{1-6}$ alkyl group, such as a methyl group, ethyl group, n-propyl group, isopropyl group, n-butyl group, isobutyl group, n-hexyl group. The $R_3$ and $R_4$ may be linked directly to form a $C_{2-6}$ alkylene group, preferably ethylene group or trimethylene group. When $R_3$ and $R_4$ are the ethylene group,

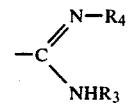

forms an imidazoline ring. And when they are a trimethylene group, it forms a pyrimidine ring.

Exemplary isoquinolinesulfonamide derivative of the invention include:

(1) N-Guanidino-5-isoquinolinesulfonamide [referred to as "Compound (1)"];

(2) N-(2-Guanidinoethyl)-5-isoquinolinesulfonamide [referred to as "Compound (2)"];

(3) N-(3-Guanidinopropyl)-5-isoquinolinesulfonamide [referred to as "Compound (3)"];

(4) N-(4-Guanidinobutyl)-5-isoquinolinesulfonamide [referred to as "Compound (4)"];

(5) N-(5-Guanidinopentyl)-5-isoquinolinesulfonamide [referred to as "Compound (5)"];

(6) N-(6-Guanidinohexyl)-5-isoquinolinesulfonamide [referred to as "Compound (6)"];

(7) N-(8-Guanidinooctyl)-5-isoquinolinesulfonamide [referred to as "Compound (7)"];

(8) N-(10-Guanidinodecyl)-5-isoquinolinesulfonamide [referred to as "Compound (8)"];

(9) N-[(2-Guanidino-1-methyl)ethyl]-5-isoquinolinesulfonamide [referred to as "Compound (9)"];

(10) N-[(1-Guanidinomethyl)propyl]-5-isoquinolinesulfonamide [referred to as "Compound (10)"];

(11) N-[(1-Guanidinomethyl)butyl]-5-isoquionolinesulfonamide [referred to as "Compound (11)"];

(12) N-[(1-Guanidinomethyl-2-methyl)propyl]-5-isoquinolinesulfonamide [referred to as "Compound (12)"];

(13) N-[(1-Guanidinomethyl)pentyl]-5-isoquinolinesulfonamide [referred to as "Compound (13)"];

(14) N-[(2,2-Dimethyl-1-quanidinomethyl)propyl]-5-isoquinolinesulfonamide [referred to as "Compound (14)"];

(15) N-[(1-Guanidinomethyl-2-methyl)butyl]-5-isoquinolinesulfonamide [referred to as "Compound (15)"];

(16) N-(2-Guanidinopropyl)-5-isoquinolinesulfonamide [referred to as "Compound (16)"];

(17) N-(2-Guanidinobutyl)-5-isoquinolinesulfonamide [referred to as "Compound (17)"];

(18) N-(2-Guanidinopentyl)-5-isoquinolinesulfonamide [referred to as "Compound (18)"];

(19) N-(2-Guanidino-3-methylbutyl)-5-isoquinolinesulfonamide [referred to as "Compound (19)"];

(20) N-(2-Guanidinohexyl)-5-isoquinolinesulfonamide [referred to as "Compound (20)"];

(21) N-(2-Guanidino-3-methylpentyl)-5-isoquinolinesulfonamide [referred to as "Compound (21)"];

(22) N-[(3,3-Dimethyl-2-quanidino)butyl]-5-isoquinolinesulfonamide [referred to as "Compound (22)"];

(23) N-(2-Guanidino-1-phenylethyl)-5-isoquinolinesulfonamide [referred to as "Compound (23)"];

(24) N-(2-Guanidino-1-benzylethyl)-5-isoquinolinesulfonamide [referred to as "Compound (24)"];

(25) N-(2-Guanidino-2-phenylethyl)-5-isoquinolinesulfonamide [referred to as "Compound (25)"];

(26) N-(2-Guanidino-3-phenylpropyl)-5-isoquinolinesulfonamide [referred to as "Compound (26)"];

(27) N-(3-Guanidino-1-methylpropyl)-5-isoquinolinesulfonamide [referred to as "Compound (27)"];

(28) N-(3-Guanidino-2-methylpropyl)-5-isoquinolinesulfonamide [referred to as "Compound (28)"];

(29) N-(3-Guanidinobutyl)-5-isoquinolinesulfonamide [referred to as "Compound (29)"];

(30) N-(3-Guanidino-1-phenylpropyl)-5-isoquinolinesulfonamide [referred to as "Compound (30)"];

(31) N-(3-Guanidino-2-phenylpropyl)-5-isoquinolinesulfonamide [referred to as "Compound (31)"];

(32) N-(3-Guanidino-3-phenylpropyl)5-isoquinolinesulfonamide [referred to as "Compound (32)"];

(33) N-(3-Guanidino-1-benzylpropyl)-5-isoquinolinesulfonamide [referred to as "Compound (33)"];

(34) N-(3-Guanidino-2-benzylpropyl)-5-isoquinolinesulfonamide [referred to as "Compound (34)"];

(35) N-(3-Guanidino-4-phenylbutyl)-5-isoquinolinesulfonamide [referred to as "Compound (35)"];

(36) N-(4-Guanidino-3-methylbutyl)-5-isoquinolinesulfonamide [referred to as "Compound (36)"];

(37) N-(4-Guanidino-3-phenylbutyl)-5-isoquinolinesulfonamide [referred to as "Compound (37)"];

(38) N-(5-Guanidino-4-benzylpentyl)-5-isoquinolinesulfonamide [referred to as "Compound (38)"];

(39) N-(5-Guanidino-2-benzylpentyl)-5-isoquinolinesulfonamide [referred to as "Compound (39)"];

(40) N-(5-Guanidino-3-phenylpentyl)-5-isoquinolinesulfonamide [referred to as "Compound (40)"];

(41) N-(2-Guanidino-1-methylpropyl)-5-isoquinolinesulfonamide [referred to as "Compound (41)"];

(42) N-(3-Guanidino-1-methylbutyl)-5-isoquinolinesulfonamide [referred to as "Compound (42)"];

(43) N-(6-Guanidino-1-methylheptyl)-5-isoquinolinesulfonamide [referred to as "Compound (43)"];

(44) 4-Amidino-1-(5-isoquinolinesulfonyl)piperazine [referred to as "Compound (44)"];

(45) 4-Amidino-1-(5-isoquinolinesulfonyl)homopiperazine [referred to as "Compound (45)"];

(46) 4-Amidino-1-(5-isoquinolinesulfonyl)-3-methylpiperazine [referrred to as ("Compound (46)"];

(47) 4-Amidino -1-(5-isoquinolinesulfonyl)-2-methylpiperazine [referred to as "Compound (47)"];

(48) 4-Amidino-1-(5-isoquinolinesulfonyl)-2-isobutylpiperazine [referred to as "Compound (48)"];

(49) 4-Amidino-2,5-dimethyl-1-(5-isoquinolinesulfonyl) piperazine [referred to as "Compound (49)"];

(50) 2-[2-(5-Isoquinolinesulfonamide)ethylamino]-2-imidazoline [referred to as "Compound (50)"];

(51) 2-[2-(5-Isoquinolinesulfonamide)ethylamino]-1,4,5,6-tetrahydropyrimidine [referred to as "Compound (51)"];

(52) N-[2-(3-Methylguanidino)ethyl]-5-isoquinolinesulfonamide [referred to as "Compound (52)"];

(53) N-[2-(2,3-Dimethylguanidino)ethyl]-5-isoquinolinesulfonamide [referred to as "Compound (53)"];

(54) N-[2-(2,3-Diethylguanidino)ethyl]-5-isoquinolinesulfonamide [referred to as "Compound (54)"];

(55) N-[2,(3-Ethylguanidino)ethyl]-5-isoquinolinesulfonamide [referred to as "Compound (55)"].

The acid addition salts of the isoquinolinesulfonamide derivatives of Formula (I) according to this invention are pharmaceutically acceptable non-toxic salts and can be prepared by conventional methods.

Suitable examples of such pharmaceutically acceptable acid addition salts include the salts of inorganic acids such as hydrochloric acid, hydrobromic acid, phosphoric acid, and sulfuric acid; and the salts of organic acids such as acetic acid, citric acid, tartaric acid, lactic acid, succinic acid, fumaric acid, maleic acid, methanesulfonic acid and p-toluenesulfonic acid.

The isoquinolinesulfonamide derivatives of Formula (I) of this invention can be prepared in accordance with the following equation.

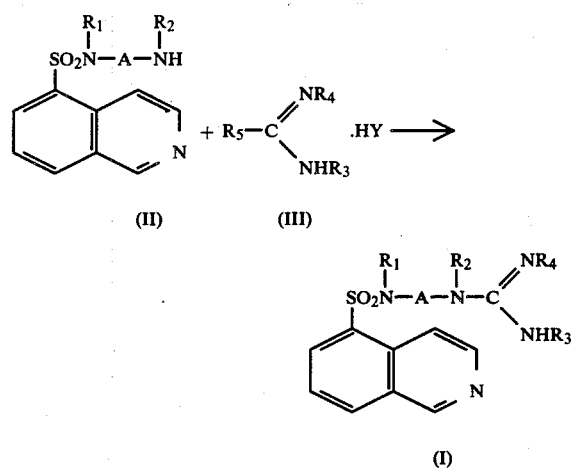

wherein A, $R_1$, $R_2$, $R_3$ and $R_4$ are the same as defined above in Formula (I), $R_5$ is a halogen atom, $R_6$—O— or $R_6$—S— ($R_6$ is alkyl group) and Y is an acid residue, preferably a pharmaceutically acceptable acid residue.

Exemplary compounds of Formula (III) include S-methylisothiourea sulfate, O-methylisourea sulfate, chloroformamidine hydrochloride, bromoformamidine hydrobromide, S-ethylisothiourea hydrobromide, S-methylisothiourea hydroiodide, O-ethylisourea sulfate, 1,2,3-trimethylisourea hydroiodide, 1,2,3-trimethylisothiourea hydroiodide, 1,3-dimethyl-2-ethylisothiourea hydroiodide, 1,2,3-triethylisothiourea hydroiodide, 2- methylthio-2-imidazoline hydroiodide and 2-methylthio-1,4,5,6-tetrahydropyrimidine. Above material compounds (II) can be prepared by method (A) or method (B) as follows;

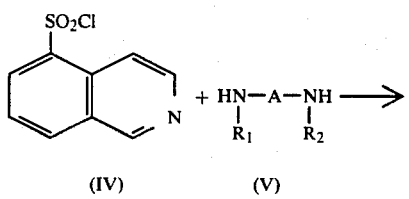

Method (A)

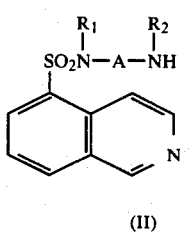

(II)

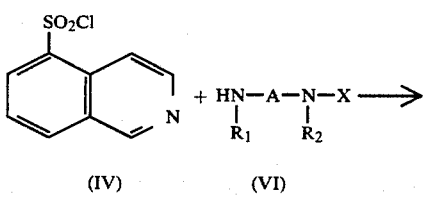

Method (B)

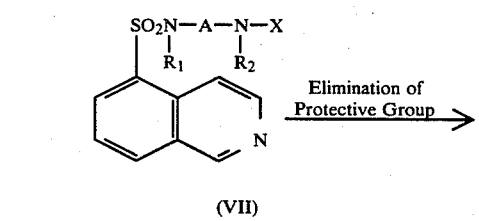

Elimination of Protective Group →

(VII)

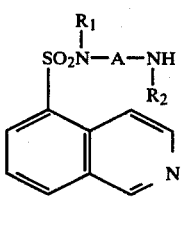

(II)

wherein A, $R_1$ and $R_2$ are the same as defined above, X is a protective group.

Exemplary compounds of Formula (V) include hydrazine, 1,2-diaminoethane, 1,3-diaminopropane, 1,4-diaminobutane, 1,5-diaminopentane, 1,6-diaminohexane, 1,8-diaminooctane, 1,10-diaminodecane, 1,3-diamino-2-phenylpropane, 1,3-diamino-2-benzylpropane, 1,5-diamino-3-methylpentane, 2,3-diaminobutane, 2,4-diaminopentane, 2,7-diaminooctane, piperazine, homopiperazine, 2-methylpiperazine and 2,5-dimethylpiperazine.

Exemplary protective groups of compound of Formula (VI) include formyl group, acetyl group, benzyl group, benzyloxycarbonyl group and t-butoxycarbonyl group.

Exemplary compounds of Formula (VI) include 2-amino-1-benzyloxycarbonylaminopropane, 2-amino-1-benzyloxycarbonylaminobutane, 2-amino-1-benzyloxycarbonylaminohexane, 2-amino-1-benzyloxycarbonylamino-2-phenylethane, 2-amino-1-benzyloxycarbonylamino-3-phenylpropane, 2-acetamido-1-aminopropane, 2-acetamido-1-amino-3-methylbutane, 2-acetamido-1-amino-2-phenylethane, 2-acetamido-1-amino-3-phenylpropane, 2-amino-1-formamido-3-phenylpropane, 2-amino-1-t-butoxycarbonylamino-3-phenylpropane, 1-amino-3-benzamido-3-phenylpropane, 1-acetamido-3-amino-4-phenylbutane, 1-amino-3-benzyloxycarbonylamino-1-phenylpropane, 1-amino-4-t-butoxycarbonylamino-3-phenylbutane, 1-amino-4-t-butoxycarbonylamino-3-methylbutane, 1-amino-5-t-butoxycarbonylamino-4-benzylpentane and 1-amino-5-t-butoxycarbonylamino-2-benzylpentane.

The reaction between the compound of Formula (IV) and the compound of Formula (VI) can be carried out in the presence or absence of an acid acceptor. Exemplary acid acceptors which can be employed include alkali metal compounds such as a hydroxide, bicarbonate, carbonate, hydride or an alkoxide, e.g. sodium bicarbonate, sodium carbonate, potassium carbonate, sodium hydroxide, potassium hydroxide, sodium hydride and sodium alkoxides such as sodium methoxide and organic tertiary amines such as trimethylamine, triethylamine, triethylenediamine and pyridine.

In general, this reaction is carried out in the presence of a reaction medium. Exemplary reaction media which can be employed include halogenated hydrocarbons such as chloroform and dichloromethane; alcohols such as methanol and ethanol; ethers such as tetrahydrofuran, diethylether, dioxane; N,N-dimethylformamide, dimethyl sulfoxide, acetonitrile.

The amount of the compound of Formula (VI) preferably ranges from 1 to 10 mols, more preferably from 1 to 3 mols per mol of the compound of Formula (IV) when the acid acceptor is present, and preferably from 2 to 20 mols, more preferably from 2 to 10 mols per mol of the compound of Formula (IV) when the acid acceptor is absent.

The amount of the acid acceptor employed is preferably about 1 to about 10 equivalents and more preferably about 1 to about 6 equivalents for each mol of the compound of Formula (IV).

The reaction between the compound of Formula (IV) and the compound of Formula (VI) can be carried out typically at a temperature of from about $-30°$ C. to about $150°$ C. and preferably from about $0°$ C. to about $120°$ C. and more preferably from about $0°$ C. to about $80°$ C.

The reaction time which can be employed is typically about 0.5 to about 72 hours and preferably about 1 to about 5 hours.

The method of obtaining the compound of Formula (II) from the compound of Formula (VII) may vary depending upon the protective group of X selected, generally known methods can be employed in this invention. For example, when the protective group of X is an acyl group such as formyl acetyl or benzoyl, the desired compounds can be obtained by hydrolysis with an acid or an alkali. When the protective group of X is an alkyloxycarbonyl group such as tert-butoxycarbonyl, the desired products can be obtained by hydrolysis with an acid. When the protective group of X is an arylmethyloxycarbonyl group such as benzyloxycarbonyl, the desired compounds can be obtained by hydrogenation or hydrolysis with an acid.

The reaction between the compound of Formula (IV) and the compound of Formula (V) can be carried out under the same condition as the reaction between the compound of Formula (IV) and the compound of Formula (VI) except that the amount of the compound of Formula (V) preferably ranges from 2 to 10 mols 1 more preferably from 2 to 4 mols per mol the compound of Formula (IV) when the acid acceptor is present, and preferably from 3 to 20 mols, more preferably from 3 to 7 mols per mol of the compound of Formula (IV) when the acid acceptor is absent.

In general, the reaction between the compound of Formula (II) and the compound of Formula (III) can be carried out in the presence of an acid acceptor. Exemplary acid acceptors which can be employed include alkali metal compounds such as a sodium bicarbonate, sodium carbonate, potassium carbonate and sodium hydroxide, organic tertiary amines such as trimethylamine, triethylamine, triethylenediamine and pyridine.

In general, this reaction is carried out in the presence of a reaction medium. Exemplary reaction media which can be employed include water and alkanols such as methanol and ethanol, or their mixture with water; mixture of the ethers such as tetrahydrofuran and dioxane, and water. The mixture rate (V/V) of water against alkanols or ethers is preferably from 20 percent to 100 percent.

The amount of the acid acceptor employed is preferably about 1 to about 10 equivalents and more preferably about 1 to 4 equivalents for each mol of the compound of Formula (II) in the reaction between the compound of Formula (II) and the compound of Formula (III).

The amount of the compound of Formula (III) is at least 1 mol, preferably from 1 to 10 mols, more preferably from 2 to 4 mols per mol of the compound of Formula (II).

The reaction between the compound of Formula (II) and the compound of Formula (III) can be carried out preferably at a temperature of from about 20° C. to about 150° C. and more preferably from about 50° C. to about 120° C.

The reaction time which can be employed is preferably about 2 to about 6 hours.

Also, the compound of Formula (I) can be prepared by the following equations:

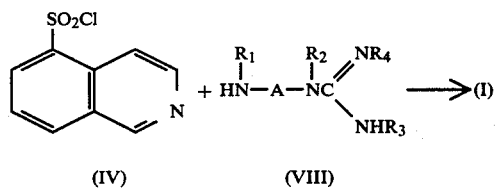

(IV)         (VIII)

wherein A, $R_1$, $R_2$, $R_3$ and $R_4$ are the same as defined above in Formula (I).

Exemplary compounds of the Formula (VIII) include 2-guanidinoethylamine, 3-guanidinopropylamine, 4-guanidinobutylamine, 3-guanidino-2-phenylpropylamine, 6-guanidinohexylamine, 1-amidinopiperazine, 1-amidino-2,5-dimethylpiperazine, 1-amidino-3-methylpiperazine and 1-amidinohomopiperazine.

The compounds of the Formula (VIII) can be easily prepared from corresponding diamine and the compound of the Formula (III). For example, 2-guanidinoethylamine can be prepared from 1,2-diaminoethane and S-methylisothiourea, and 1-amidinopiperadine can be prepared from piperazine and S-methylisothiourea.

The amount of the compound of Formula (VIII) is at least 1 mol, preferably 1 to about 10 mols per mol of the compound of Formula (IV).

In general, the reaction between the compound of Formula (IV) and the compound of Formula (VIII) can be carried out in the presence of an acid acceptor. Exemplary acid acceptors which can be employed include alkali metal compounds such as sodium bicarbonate, sodium carbonate, potassium carbonate, sodium hydroxide, potassium hydroxide, sodium hydride, sodium methoxide; and organic tertiary amines such as trimethylamine, triethylamine, triethylenediamine and pyridine.

In general, this reaction is carried out in the presence of a reaction medium. Exemplary reaction media which can be employed include water and alkanols such as methanol and ethanol, or their mixture with water; mixture of ethers such as tetrahydrofuran, dioxane, N,N-dimethylformamide and acetone, and water.

The mixture rate (V/V) of water against alcohols or ethers is preferably from 20 percent to 100 percent.

The amount of the acid acceptor employed is preferably about 1 to about 10 equivalents and more preferably about 1 to about 4 equivalents for each mol of the compound of Formula (IV) in the reaction between the compound of Formula (IV) and the compound of Formula (VIII).

The reaction between the compound of Formula (IV) and the compound of Formula (VIII) can be carried out typically at a temperature of from about −30° C. to about 150° C., preferably from about −10° C. to about 80° C. and more preferably from about 0° C. to about 30° C.

The reaction time which can be employed is typically about 0.5 to about 72 hours and preferably about 1 to about 5 hours.

It has now been found that the isoquinolinesulfonamide derivatives of Formula (I) and the pharmaceutically acceptable salts have pharmacologically and biochemically interesting properties such as a relaxatory action for vascular smooth muscle, an action for increasing blood flow and hypotensive action and are useful as a vasodilator, a hypotensor, an ameliorant of cerebral circulation, a medicine for angina pectoris and a preventive and a medicine for cardiovascular thrombosis.

The effect of the isoquinolinesulfonamide derivatives and the pharmaceutically acceptable acid addition salts of this invention on smooth muscle can be proved by suspending a mesenteric artery taken out from a rabbit in a helical form, contracting the mesenteric artery with potassium chloride and adding the isoquinolinesulfonyl derivatives or their pharmaceutically acceptable acid addition salts of this invention to the contracted mesenteric artery, resulting in the relaxation of the mesenteric artery. When, for example, N-(2-guanidinoethyl)-5-isoquinolinesulfonamide, i.e., compound (2) was added and a complete relaxation was designated 100%, the concentration which could bring about a relaxation of 50%, i.e., $ED_{50}$ was 1 μM.

The effect of the isoquinolinesulfonamide derivatives and the pharmaceutically acceptable acid addition salts of this invention on the vasodilatation of the femoral and vertebral arteries can be measured by anesthetizing a dog of mixed breed weighing 8 to 15 Kg by an intravenous administration of 35 mg/Kg of pentbarbital, Providing an acute type probe (a product of Nippon Koden K.K., Japan) with the femoral and vertebral arteries, administering the isoquinolinesulfonamide derivatives and the pharmaceutically acceptable acid addition salts to the femoral vein through a polyethylene tube inserted into the femoral vein side chain and measuring the blood flow volume with an electromagnetic flowmeter (a product of Nippon Koden K.K., Japan, "MFV-1200"). 1 mg/Kg of N-(2-guanidinoethyl)-5-isoquinolinesulfonamide, i.e., Compound (2) was intravenously administered, the increased blood flow volumes in the vertebral artery and in the femoral artery were 95% and 37%. And the duration time is more than 30 minutes.

Furthermore, when another isoquinolinesulfonamide derivatives and the pharmaceutically acceptable acid addition salts of this invention were intravenously and arterially administered for the above described purposed, remarkable increase of blood flow could be observed. Also remarkable and durable hypotensive action could be observed, and blood pressure of 32 mmHg decreased at advantage of blood pressure. The action continued more than 30 minutes.

When the toxity test of the compound of this invention was done by using rats and mice, any remarkable toxity against the center, the kidney and the liver could not be observed.

For example, the acute toxicity of N-(2-guanidinoethyl)-5-isoquinolinesulfonamide i.e., Compound (2) i.e., $LD_{50}$ was 59 mg/Kg in giving male ddY-strain mice an intravenous administration.

The following examples illustrate the present invention in more detail, but they are given for illustration purposes only and are not to be construed as limiting the invention.

of N-(2-aminoethyl)-5-isoquinolinesulfonamide as an oily substance in a yield of 66%.

The same procedures as described above were repeated using the compounds of Formula (V) as set forth in Table 1 under the reaction conditions as set forth in Table 1, and N-(ω-aminoalkyl)-5-isoquinolinesulfonamide as set forth in Table 1 were obtained.

The equation is as follows;

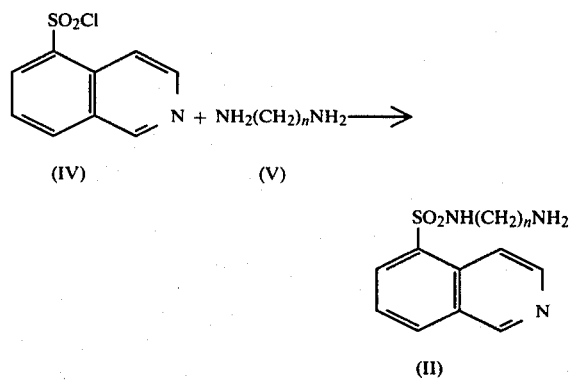

TABLE 1

| Run No. | SO₂Cl-isoquinoline (g) | Compound of Formula (V) | (g) | Reaction Temperature (°C.) | Reaction Time (hour) | n | SO₂NH(CH₂)ₙNH₂-isoquinoline Yield [g] | (%) |
|---|---|---|---|---|---|---|---|---|
| 1 | 3.41 | H₂N(CH₂)₃NH₂ | 11.1 | 20~25 | 2 | 3 | 2.9 | (73) |
| 2 | 4.55 | H₂N(CH₂)₄NH₂ | 11.0 | " | 2 | 4 | 3.46 | (62) |
| 3 | 4.55 | H₂N(CH₂)₅NH₂ | 11.5 | " | 3 | 5 | 4.16 | (71) |
| 4 | 4.55 | H₂N(CH₂)₆NH₂ | 11.6 | " | 5 | 6 | 4.6 | (75) |
| 5 | 4.0 | H₂N(CH₂)₈NH₂ | 13.0 | " | 4 | 8 | 3.83 | (65) |
| 6 | 2.28 | H₂N(CH₂)₁₀NH₂ | 8.62 | " | 10 | 10 | 2.2 | (61) |

REFERENTIAL EXAMPLE 1

In 200 ml of chloroform was dissolved 12.0 g of 1,2-diaminoethane, and to the solution was added dropwise 100 ml of a chloroform solution containing 4.55 g of 5-isoquinolinesulfonyl chloride under cooling with ice. After the dropwise addition of the chloroform solution, the mixed solution was stirred at a temperature of 20° C. to 25° C. for two hours, and then the reaction solution was extracted with a 10% aqueous hydrochloric acid solution. The pH of the aqueous layer was adjusted to 10 with a 10% aqueous sodium hydroxide solution, and the aqueous layer was extracted with chloroform. The chloroform layer extracted was washed with water and dried with anhydrous potassium carbonate. Then the chloroform was distilled from the chloroform layer, and the residue obtained was subjected to a column chromatography [silica gel: 200 g; developing solvent: 2% methanol/chloroform (volume ratio)] to give 3.3 g

REFERENTIAL EXAMPLE 2

In 50 ml of a chloroform solution containing 11.55 g of 1,3-diamino-2-phenylpropane and 1.33 g of triethylamine was added dropwise 30 ml of a chloroform solution containing 3.5 g of 5-isoquinolinesulfonyl chloride under cooling with ice. After the dropwise addition of the chloroform solution, the mixed solution was stirred at a temperature of 10° C. to 20° C. for four hours, and the reaction mixture solution was washed with water and dried with anhydrous potassium carbonate. After the chloroform was distilled therefrom, the residue thus obtained was subjected to a silica gel column chromatography (silica gel: 90 g; solvent: 5% methanol/chloroform (volume ratio)) to give 3.20 g of N-(3-amino-2-phenylpropyl)-5-isoquinolinesulfonamide in a yield of 61%.

The same procedures as described above were repeated using the compounds of Formula (V) as set forth in Table 2-1 under the reaction conditions as set forth in Table 2-1, and compounds as set forth in Table 2-2 were obtained.

The equation is as follows;

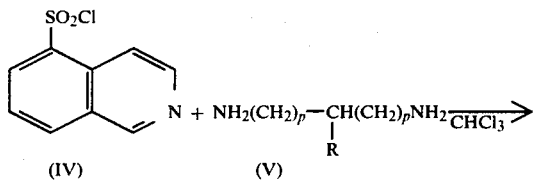

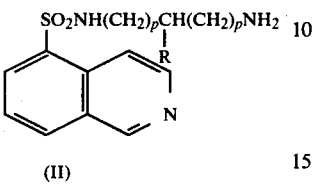

trated to dryness to give 1.30 g of N-(2-amino-1-methylethyl)-5-isoquinolinesulfonamide in a yield of 98%.

The same procedures as described above were repeated by using the compounds of Formula (VI) as set forth in Table 3 under the reaction conditions as set forth in Table 3 and 4, and compounds as set forth in Table 3 and 4 were obtained.

The equation is as follows;

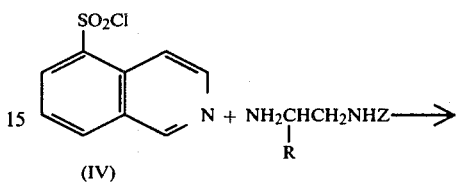

TABLE 2

| Run No. | SO₂Cl-isoquinoline (g) | Compound of Formula (V) (g) | Acid acceptor (g) | Reaction Temperature (°C.) | Reaction Time (hour) | P | R | Yield [g (%)] |
|---|---|---|---|---|---|---|---|---|
| 1 | 4.0 | NH₂CH₂CHCH₂NH₂ \| CH₃  6.96 | K₂CO₃ 6.06 | 5~10 | 4 | 1 | CH₃ | 3.43 (70) |
| 2 | 4.0 | NH₂CH₂CHCH₂NH₂ \| CH₂Ph  11.53 | NEt₃ 7.10 | 20~25 | 5 | 1 | CH₂Ph | 4.17 (67) |

REFERENTIAL EXAMPLE 3

In 20 ml of a chloroform solution containing 2.23 g of 2-benzyloxycarbonylamino-1-methylethylamine and 1.2 g of triethylamine was added dropwise 20 ml of a chloroform solution containing 1.80 g of 5-isoquinolinesulfonyl chloride under cooling with ice. After the dropwise addition of the chloroform solution, the mixed solution was stirred at a temperature of 20° C. to 25° C. for two hours, and the reaction mixture solution was washed with water and dried with anhydrous magnesium sulfate. The chloroform was distilled therefrom under reduced pressure. The crystalline residue thus obtained was recrystallized from ethanol to give 2.68 g of N-(2-benzyloxycarbonylamino-1-methylethyl)-5-isoquinolinesulfonamide in a yield of 85%.

In 50 ml of ethanol was dissolved 2.0 g of N-(2-benzyloxycarbonylamino-1-methylethyl)-5-isoquinolinesulfonamide obtained above, and to the solution was added 0.1 g of 5% palladium-carbon. Then the solution was stirred at a temperature of 15° C.~25° C. in a hydrogen (0.7 to 1.40 kg/cm²) for 3 hours. The palladium-carbon was separated from the reaction solution by filtration under the reduced pressure. After the methanol was distilled therefrom, the reaction solution was concen-

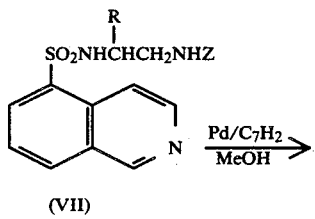

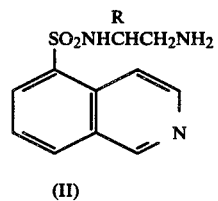

wherein Z represents

—COCH₂Ph.

TABLE 3

| Run No. | SO₂Cl-isoquinoline (g) | R | NH₂CHCH₂NHZ / R (g) | NEt₃ (g) | Reaction Temperature (°C.) | Reaction Time (hour) | Yield (VII) [g | (%)] |
|---|---|---|---|---|---|---|---|---|
| 1 | 4.0 | Et | 4.28 | 2.13 | 20~25 | 3 | 6.38 | (88) |
| 2 | 3.5 | n-Bu | 4.61 | 2.02 | 20~25 | 2 | 5.89 | (87) |
| 3 | 3.0 | Ph | 3.91 | 1.73 | 0~10 | 4 | 5.10 | (84) |
| 4 | 3.0 | —CH₂Ph | 4.4 | 1.86 | 0~10 | 5 | 5.56 | (89) |

TABLE 4

| Run No. | R | (VII) (g) | 5% Pd/C (g) | Reaction Temperature (°C.) | Reaction Time (hour) | Yield (II) [g | (%)] |
|---|---|---|---|---|---|---|---|
| 1 | Et | 5.0 | 0.1 | 20~25 | 4 | 3.34 | (99) |
| 2 | n-Bu | " | " | " | 3 | 3.41 | (98) |
| 3 | Ph | " | " | " | 2 | 3.44 | (97) |
| 4 | —CH₂Ph | " | " | " | 2 | 3.52 | (98) |

REFERENTIAL EXAMPLE 4

In 50 ml of a chloroform solution containing 2.0 g of 2-acetylaminopropylamine and 2.6 g of triethylamine was added dropwise 50 ml of a chloroform solution containing 3.28 g of 5-isoquinolinesulfonyl chloride under cooling with ice. The mixed solution was stirred at a temperature of 15° C. to 25° C. for two hours, and then the reaction solution was washed with water and dried with anhydrous sodium sulfate. The chloroform was distilled therefrom under reduced pressure. The crystalline residue thus obtained was recrystallized from methanol to give 3.67 g of N-(2-acetylaminopropyl)-5-isoquinolinesulfonamide in a yield of 83%.

In 50 ml of 10% hydrochloride was dissolved 3.0 g of N-(2-acetylaminopropyl)-5-isoquinolinesulfonamide as obtained above, and the mixture was stirred at a temperature of 90° C. to 100° C. for 36 hours. The reaction solution was washed with chloroform, rendered alkaline with 1N sodium hydroxide and extracted with chloroform. The chloroform layer was washed with water, dried with anhydrous magnesium sulfate, and the chloroform was distilled therefrom under reduced pressure. The residue thus obtained was subjected to an alumina column chromatography (alumina: 70 g; solvent: chloroform) to give 1.44 g of N-(2-aminopropyl)-5-isoquinolinesulfonamide in a yield of 56%.

The same procedures as described above were repeated using the compounds Formula (IV) as set forth in Table 5 under the reaction conditions as set forth in Table 5 and 6, and there obtained N-(2-amino-3-methylbutyl)-5-isoquinolinesulfonamide, N-(2-amino-2-phenylethyl)-5-isoquinolinesulfonamide and N-(2-amino-3-phenylpropyl)-5-isoquinolinesulfonamide.

The equation is as follows;

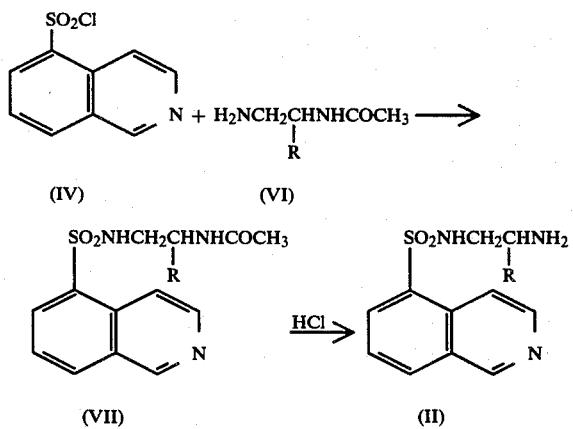

TABLE 5

| Run No. | SO₂Cl-isoquinoline (g) | H₂NCH₂CHNHCOCH₃ R | (g) | Et₃N (g) | Reaction Temperature (°C.) | Reaction Time (hour) | Yield [g | (%)] |
|---|---|---|---|---|---|---|---|---|
| 1 | 4.0 | i-Pr | 2.8 | 2.66 | 20~25 | 2 | 5.19 | (88) |
| 2 | " | Ph | 3.75 | " | 10~20 | " | 5.83 | (90) |
| 3 | " | PhCH₂ | 4.04 | " | 10~20 | " | 5.64 | (84) |

TABLE 6

| Run No. | R | (VII) (g) | Concentration of HCl (ml) | Reaction Temperature (°C.) | Reaction Time (hour) | Yield [g | (g)] |
|---|---|---|---|---|---|---|---|
| 1 | iPr | 5.0 | 10% (70) | 90~100 | 24 | 2.63 | (60) |
| 2 | Ph | " | 10% (70) | " | " | 2.92 | (66) |
| 3 | PhCH₂ | " | 10% (70) | " | " | 2.23 | (50) |

REFERENTIAL EXAMPLE 5

The same procedure as described in Referential example 3 were repeated using 4.0 g of 5-isoquinolinesulfonyl chloride, 6.95 g of 4-t-butoxycarbonylamino-3-phenylbutylamine and 2.66 g of triethylamine, and there were obtained 6.6 g of N-(4-t-butoxycarbonylamino-3-phenylbutyl)-5-isoquinolinesulfonamide in a yield of 83%.

In 30 ml of trifluoroacetic acid was dissolved 6.0 g of N-(4-t-butoxycarbonylamino-3-phenylbutyl)-5-isoquinolinesulfonamide, and left at a temperature of 20° C.~25° C. for 30 minutes. The mixrure was condensed under reduced pressure. To the reaction solution was added ethyl ether, and the crystals precipitated were separated by filtration. The crystals thus obtained were washed with ethylether to give 4.54 g of N-(4-amino-3-phenylbutyl)-5-isoquinolinesulfonamide in a yield of 97%.

The same procedures as described above were repeated using the compounds of Formula (VI) as set forth in Table 7 under the reaction conditions as set in Table 7 and 8, and there were obtained N-(4-amino-3-methylbutyl)-5-isoquinolinesulfonamide, N-(5-amino-4-benzylpentyl)-5-isoquinolinesulfonamide and N-(5-amino-2-benzypentyl)-5-isoquinolinesulfonamide.

The equation is as follows;

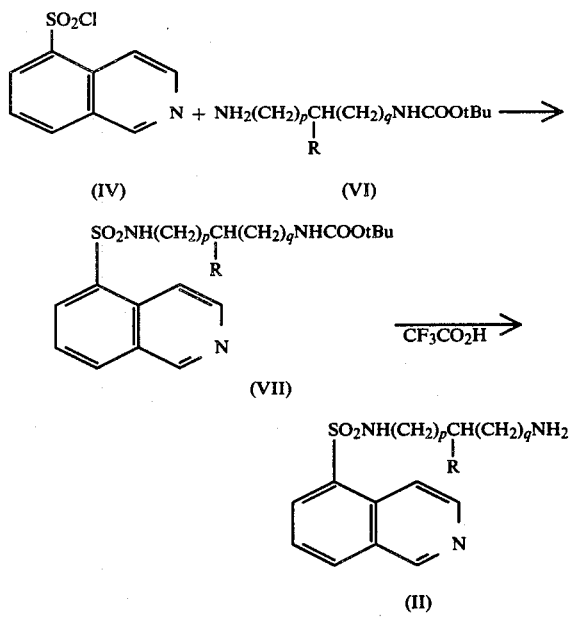

TABLE 7

| Run No. | (IV) (g) | p q | R | (VI) (g) | NEt₃ (g) | Reaction Temperature(°C.) Reaction Time (hour) | Compound of Formula (VII) Yield [g | (%)] |
|---|---|---|---|---|---|---|---|---|
| 1 | 3.0 | 2 1 | CH₃ | 3.47 | 2.0 | 20~25 2 | 4.55 | (88) |
| 2 | " | 3 | PhCH₂ | 4.63 | " | 20~25 | 5.34 | (84) |

TABLE 7-continued

| | SO₂Cl-isoquinoline (IV) | | NH₂(CH₂)ₚCH(CH₂)ᵩNHCOOtBu with R (VI) | | | Reaction Temperature(°C.) | Compound of Formula (VII) Yield | |
|---|---|---|---|---|---|---|---|---|
| Run No. | (g) | p q | R | (g) | NEt₃ (g) | Reaction Time (hour) | [g | (%)] |
| 3 | " | 1 1 3 | PhCH₂ | 4.63 | " | 2 20~25 2 | 5.53 | (87) |

TABLE 8

| | SO₂NH(CH₂)ₚCH(CH₂)ᵩNHCOOtBu-isoquinoline (VII) | | | | Reaction Temperature (°C.) | Reaction Time (Min.) | SO₂NH(CH₂)ₚCH(CH₂)ᵩNH₂-isoquinoline (II) Yield | |
|---|---|---|---|---|---|---|---|---|
| Run No. | p q | R | (g) | | | | [g | (%)] |
| 1 | 2 1 | CH₃ | 4 | | 20~25 | 30 | 2.96 | (99) |
| 2 | 3 1 | PhCH₂ | 5 | | " | " | 3.43 | (87) |
| 3 | 1 3 | PhCH₂ | 5 | | " | " | 3.73 | (94) |

REFERENTIAL EXAMPLE 6

In 100 ml of chloroform was dissolved 12.9 g of 2,3-diaminobutane and to the solution was added dropwise 10 ml of a chloroform solution containing 4.0 g of 5-isoquinolinesulfonyl chloride under cooling with ice. After the dropwise addition of the chloroform solution, the mixed solution was stirred at a temperature of 20° C. to 25° C. for two hours, and the reaction mixture solution was washed with water and dried with anhydrous sodium carbonate. The chloroform was distilled therefrom under reduced pressure, and the residue thus obtained was subjected to a column chromatography [silica gel: 160 g; solvent: chloroform] to give 3.92 g of N-(2-amino-1-methylpropyl)-5-isoquinolinesulfonamide in a yield of 80%.

The same procedures as described above were repeated using the compounds of Formula (V) as set forth in Table 9 under the reaction conditions as set forth in Table 9, and N-(6-amino-1-methylheptyl)-5-isoquinolinesulfonamide were obtained.

The equation is as follows;

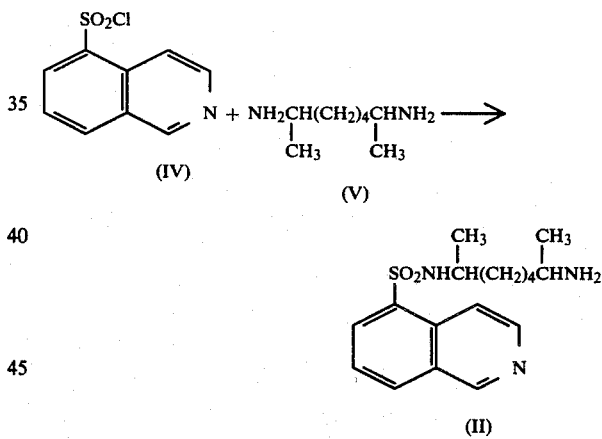

TABLE 9

| SO₂Cl-isoquinoline (IV) (g) | NH₂CH(CH₂)₄CHNH₂ with CH₃ CH₃ (g) | Reaction Temperature (°C.) | Reaction Time (hour) | SO₂NHCH(CH₂)₄CHNH₂ with CH₃ CH₃-isoquinoline Yield | |
|---|---|---|---|---|---|
| | | | | [g | (%)] |
| 4 | 16.8 | 20~25 | 3 | 5.24 | (89) |

EXAMPLE 1

In 30 ml of methanol was dissolved 3.3 g of N-(2-aminoethyl)-5-isoquinolinesulfonamide obtained in Referential example 1, and to the solution was added 25 ml of water solution containing 5.0 g of S-methylisothiourea sulfate. And to the mixed solution was added 1N aqueous sodium hydroxide solution, the mixed solution thus obtained was heated at reflux for two hours. After the reflux, the methanol was distilled therefrom under reduced pressure, and the white crystals precipitated were separated by filtration under reduced pressure. The crystalline residue thus obtained was recrystallized from methanol to give 3.24 g of N-(2-guanidinoethyl)-5-isoquinolinesulfonamide, i.e., Compound (2) in a yield of 84%.

Mass spectrum (m/e): 294 (M+1), 235, 207, 192 and 128.

NMR spectrum (D$_2$O, DCl,$\delta$): 3.0~3.3 (4H, 2×CH$_2$), 8.0~8.3 (1H), 8.7~9.1 (4H) and 9.9 (1H).

IR absorption spectrum ($\nu_{max}$, cm$^{-1}$): 3300, 3500, 1690, 1650, 1200 and 1170.

The same procedures as described above were repeated using the compounds of Formula (II) and the compounds of Formula (III) as set forth in Table 10 under the reaction conditions as set forth in Table 10, and there were obtained N-($\omega$-guanidinoalkyl)-5-isoquinolinesulfonamide as set forth in Table 11.

The equation is as follows;

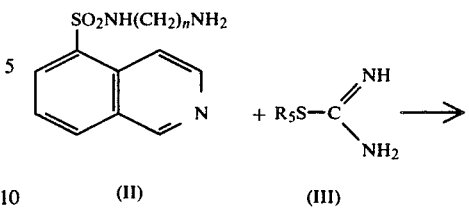

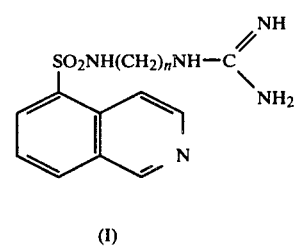

TABLE 10

| Run No. | n | SO$_2$NH(CH$_2$)$_n$NH$_2$ isoquinoline (II) (g) | R$_5$S—C(=NH)(NH$_2$) .HY (III) (g) | Acid acceptor (g) | Solvent | Reaction Temperature | Reflux Time (hour) |
|---|---|---|---|---|---|---|---|
| 1 | 3 | 1.0 | CH$_3$SC(=NH)(NH$_2$) .½H$_2$SO$_4$ 1.44 | NaOH 0.453 | H$_2$O | Reflux | 3 |
| 2 | 4 | " | CH$_3$SC(=NH)(NH$_2$) .½H$_2$SO$_4$ 1.14 | K$_2$CO$_3$ 0.98 | MeOH:H$_2$O 60:40 | " | 4 |
| 3 | 5 | " | C$_2$H$_5$SC(=NH)(NH$_2$) .HBr 1.63 | K$_2$CO$_3$ 0.82 | MeOH:H$_2$O 60:40 | " | 4 |
| 4 | 6 | " | CH$_3$SC(=NH)(NH$_2$) .½H$_2$SO$_4$ 1.45 | K$_2$CO$_3$ 0.79 | EtOH:H$_2$O 50:50 | " | 4 |
| 5 | 8 | " | CH$_3$SC(=NH)(NH$_2$) .½H$_2$SO$_4$ 1.52 | K$_2$CO$_3$ 0.62 | EtOH:H$_2$O 70:30 | " | 3 |
| 6 | 10 | " | CH$_3$SC(=NH)(NH$_2$) .½H$_2$SO$_4$ 1.26 | K$_2$CO$_3$ 0.69 | EtOH:H$_2$O 80:20 | " | 3 |

TABLE 11

SO₂NH(CH₂)ₙNHC(=NH)NH₂ attached to isoquinoline

| Run No. | Compound No. | n | Yield [g] | (%) | Mass Spectrum (m/e) | IR Absorption Spectrum ($\nu_{max}$, cm$^{-1}$) | NMR Spectrum (D₂O, DCl, δ) |
|---|---|---|---|---|---|---|---|
| 1 | 3 | 3 | 1.04 | (90) | 308, 235, 192 | 1690, 1640, 1200, 1170 | 1.5~1.7 (2H), 3.0~3.3 (4H), 8.7~9.1 (4H), 9.9 (1H), 8.0~8.3 (1H) |
| 2 | 4 | 4 | 1.03 | (89) | 322, 277, 235, 221, 207, 192 | 1680, 1640, 1200, 1160, 1050 | 1.4~1.7 (4H), 3.0~3.3 (4H), 8.7~9.1 (4H), 9.9 (1H), 8.0~8.3 (1H) |
| 3 | 5 | 5 | 1.05 | (92) | 336, 263, 249, 235, 221, 207, 192 | 1690, 1630, 1200, 1160, 1070 | 1.4~1.7 (6H), 3.0~3.3 (4H), 8.7~9.1 (4H), 9.9 (1H), 8.0~8.3 (1H) |
| 4 | 6 | 6 | 0.989 | (87) | 350, 290, 249, 235, 207, 192 | 1690, 1640, 1200, 1180, 1070 | 1.3~1.7 (8H), 3.0~3.3 (4H), 8.0~8.3 (1H), 8.7~9.1 (4H), 9.9 (1H) |
| 5 | 7 | 8 | 0.923 | (82) | 378, 319, 277, 235, 207, 192 | 1680, 1630, 1200, 1170 | 1.3~1.7 (12H), 3.0~3.3 (4H), 8.0~8.3 (1H), 8.7~9.1 (4H), 9.9 (1H) |
| 6 | 8 | 10 | 0.881 | (79) | 406, 333, 305, 235, 221, 207, 192 | 1700, 1650, 1200, 1170 | 1.3~1.7 (16H), 3.0~3.3 (4H), 8.0~8.3 (1H), 8.7~9.1 (4H), 9.9 (1H) |

EXAMPLE 2

The mixture solution of 20 ml of water and 40 ml of 2N-sodium hydroxide, containing 5.02 g of N-(2-aminoethyl)-5-isoquinolinesulfonamide obtained in Referential example 1 and 7.38 g of O-methylisourea sulfate was stirred at a temperature of 80° C. for three hours. After the reaction solution was cooled with ice, the pH of the aqueous layer was adjusted to 11 with a 2N aqueous sodium hydroxide solution. The white crystals precipitated were separated by filtration, and to the residue thus obtained was added 10 ml of a 2N aqueous hydrochloric acid solution. The pH of the solution was adjusted to 11 with a 2N aqueous sodium hydroxide solution. The crystals precipitated were separated by filtration, the crystalline residue thus obtained was washed with water and condensed to dryness to give 2.65 g of N-(2-guanidinoethyl)-5-isoquinolinesulfonamide, i.e., Compound (2) in a yield of 90%.

EXAMPLE 3

In 20 ml of a tetrahydrofuran solution containing 1.64 g of 5-isoquinolinesulfonyl chloride was added dropwise 0.9 ml of a 80% hydrazine hydrate under cooling with ice. After the dropwise addition of a hydrazine hydrate, the mixed solution obtained was stirred under cooling with ice for 1 hour. The crystals precipitated were separated, and the crystalline residue was washed with water and tetrahydrofuran. To the residue obtained was added 5 ml of methanol and 2 ml of water, and the pH of the aqueous layer was adjusted to 2 with 10% hydrochloric acid. After the methanol was distilled therefrom the crystalline residue thus obtained was recrystallized from water and methanol solution to give 1.26 g of 5-isoquinolinesulfonohydrazine in a yield of 78%.

In 20 ml of 0.5N sodium hydroxide was dissolved 1.0 g of 5-isoquinolinesulfonohydrazine obtained above and 1.53 g of S-methylisothiourea sulfate, and the mixture solution was heated at reflux for 1 hour. The sodium hydroxide was distilled under reduced pressure and to the residue thus obtained was added a 10 ml of methanol. The insoluble part was removed by filtration. After the methanol was distilled from the methanol solution, the crystalline residue thus obtained was recrystallized from methanol/ethanol to give 0.72 g of N-guanidino-5-isoquinolinesulfonamide, i.e., Compound (1) in a yield of 64%.

NMR spectrum (DMSO-d₆,δ): 7.3~8.4 (4H), 8.5 (2H) and 9.3 (1H).

IR absorption spectrum ($\nu_{max}$, cm$^{-1}$): 3420, 1680 and 1010.

EXAMPLE 4

In 30 ml of a 60% methanol/water solution (volume ratio) was dissolved 2 g of N-(3-amino-2-phenypropyl)-5-isoquinolinesulfonamide obtained Referential example 2, 2.05 g of S-methylisothiourea sulfate and 1.67 g of potassium carbonate, and the mixed solution was heated at reflux for two hours. After the reflux, the methanol was distilled therefrom under reduced pressure and the white crystalline residue the obtained was separated by filtration under reduced pressure. The residue was recrystallized from methanol to give 1.93 g of N-(3-guanidino-2-phenylpropyl)-5-isoquinolinesulfonamide, i.e., Compound (31) in a yield of 86%.

Mass spectrum (m/e): 384, 325, 311 and 207.

NMR spectrum (D₂O, DCl,δ): 2.2~2.4 (1H), 3.0~3.3 (4H), 7.2 (5H), 8.0~8.3 (1H), 8.7~9.1 (4H) and 9.9 (1H).

IR absorption spectrum ($\nu_{max}$, cm$^{-1}$): 3500, 3300, 1700, 1650, 1200, 1180 and 1040.

The same procedures as described above were repeated using the compounds of Formula (II) as set forth in Table 12 under the reaction conditions as set forth in Table 12, and there were obtained N-(3-guanidino-2-methylpropyl)-5-isoquinolinesulfonamide, i.e., Compound (28) and N-(3-guanidino-2-benzylpropyl)-5-isoquinolinesulfonamide, i.e., Compound (34) as set forth in Table 13.

The equation is as follows;

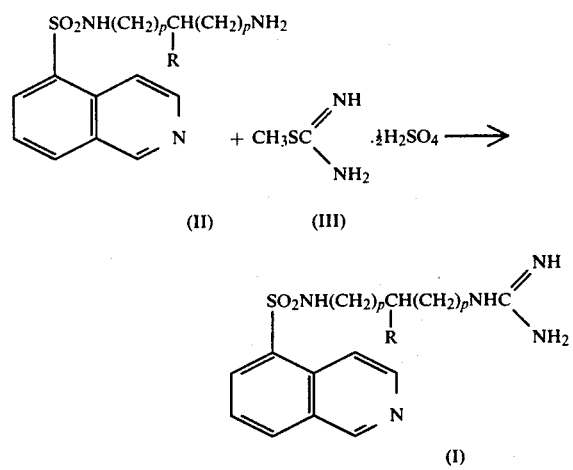

thyl)-5-isoquinolinesulfonamide, i.e., Compound (9) in a yield of 82%.

Mass spectrum (m/e): 308, 235, 207, 192 and 128.

NMR spectrum (D$_2$O, DCl,δ): 1.3~1.5 (3H), 3.0~3.3 (3H), 8.0~8.3 (1H), 8.7~9.1 (4H) and 9.9 (1H).

IR spectrum ($\nu_{max}$, cm$^{-1}$): 3500, 3300, 1690, 1630, 1360, 1180 and 1140.

The same procedure as described above were repeated using the compounds of Formula (II) as set forth in Table 14 under the reaction conditions as set forth in Table 14, and there were obtained N-[1-guanidinomethyl)propyl]-5-isoquinolinesulfonamide, i.e., Compound (10), N-[(1-guanidinomethyl)pentyl]-5-isoquinolinesulfonamide, i.e., Compound (13), N-(2-guanidino-1-phenylethyl)-5-isoquinolinesulfonamide, i.e., Compound (23) and N-(2-guanidino-1-benzylethyl)-5-isoquinolinesulfonamide, i.e., Compound (24) as set forth in Table 15.

The equation is as follows;

TABLE 12

| Run No. | P, R | (g) | Compound of Formula (III) (g) | Solvent | Acid acceptor (g) | Reaction Temperature (°C.) | Reaction Time (hour) |
|---|---|---|---|---|---|---|---|
| 1 | 1, CH$_3$ | 1.0 | 1.43 | H$_2$O | K$_2$CO$_3$ 1.11 | Reflux | 2 |
| 2 | 1, —CH$_2$Ph | " | 1.0 | EtOH:H$_2$O 40:60 | K$_2$CO$_3$ 0.894 | Reflux | 3 |

TABLE 13

| Run No. | Compound No. | n, R | Yield [g | (%)] | Mass Spectrum (m/e) | IR Absorption Spectrum ($\nu_{max}$, cm$^{-1}$) | NMR Spectrum (D$_2$O, DCl, δ) |
|---|---|---|---|---|---|---|---|
| 1 | 28 | 1, CH$_3$ | 1.09 | (95) | 322, 249 235, 207 | 1690, 1650 1200, 1170 1030 | 0.9~1.1 (3H), 2.0~2.2 (1H), 3.0~3.3 (4H), 8.0~8.3 (1H), 8.7~9.1 (4H), 9.9 (1H) |
| 2 | 34 | 1, —CH$_2$Ph | 1.01 | (90) | 398, 320 307, 221, 207 | 1680, 1650 1200, 1170 1030 | 2.0~2.4 (3H), 3.0~3.3 (4H), 7.2 (5H), 8.0~8.3 (1H), 8.7~9.1 (4H), 9.9 (1H) |

EXAMPLE 5

In 30 ml of a 60% methanol/water solution (volume ratio) was dissolved 1.0 g of N-(2-amino-1-methylethyl)-5-isoquinolinesulfonamide obtained in Referential example 3, 1.44 g of S-methylisothiourea sulfate and 0.528 g of sodium hydroxide, and the mixed solution was heated at reflux for the three hours. After the reflux, the methanol was distilled therefrom under reduced pressure, and to the reaction solution was added water so that the total volume of the solution was 30 ml. The white crystalline residue thus obtained was separated by filtration. The residue was recrystallized from methanol to give 0.95 g of N-(2-guanidino-1-methyle-

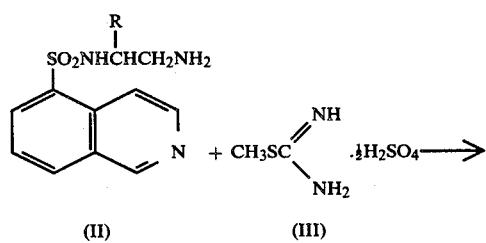

-continued

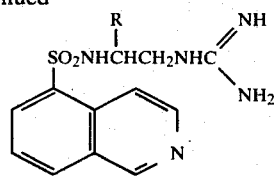

(I)

Table 16, and there were obtained N-(2-guanidino-3-methylbutyl)-5-isoquinolinesulfonamide, i.e., Compound (19), N-(2-guanidino-2-phenylethyl)-5-isoquinolinesulfonamide, i.e., Compound (25) and N-(2-guanidino-3-phenylpropyl)-5-isoquinolinesulfonamide, i.e., Compound (26) as set forth in Table 17.

The equation is as follows:

TABLE 14

| Run No. | R | R (g) | Compound of Formula (III) (g) | Solvent | Reaction Temperature | Reaction Time (hour) |
|---|---|---|---|---|---|---|
| 1 | Et | 3.0 | 3.69 | MeOH:H$_2$O 40:60 | Reflux | 2 |
| 2 | n-Bu | " | 3.95 | MeOH:H$_2$O 40:60 | " | 3 |
| 3 | Ph | " | 2.66 | MeOH:H$_2$O 70:30 | " | 3 |
| 4 | PhCH$_2$ | " | 4.10 | MeOH:H$_2$O 70:30 | " | 3 |

TABLE 15

| Run No. | Compound No. | R | Yield [g] | Yield (%) | Mass Spectrum (m/e) | IR Absorption Spectrum ($\nu_{max}$, cm$^{-1}$) | NMR Spectrum (D$_2$O, DCl, δ) |
|---|---|---|---|---|---|---|---|
| 1 | 10 | Et | 2.93 | (85) | 322, 249, 207, 192 | 1690, 1640, 1210, 1170, 1040 | 1.0~1.2 (3H), 1.6~2.0 (2H), 3.0~3.3 (3H), 8.0~8.3 (1H), 8.7~9.1 (4H), 9.9 (1H) |
| 2 | 13 | n-Bu | 3.00 | (88) | 350, 277, 207, 192 | 1700, 1640, 1210, 1170, 1040 | 0.9~1.1 (3H), 1.2~1.8 (6H), 3.0~3.3 (3H), 8.0~8.3 (1H), 8.7~9.1 (4H), 9.9 (1H) |
| 3 | 23 | Ph | 2.74 | (81) | 370, 311, 297, 207, 192 | 1710, 1660, 1210, 1180, 1040 | 3.0~3.4 (3H), 7.2 (5H), 8.0~8.3 (1H), 8.7~9.1 (4H), 9.9 (1H) |
| 4 | 24 | Ph—CH$_2$ | 3.03 | (90) | 384, 325, 311, 297, 207, 192 | 1700, 1640, 1200, 1170, 1040 | 2.1~2.3 (2H), 3.0~3.3 (3H), 7.2 (5H), 8.0~8.3 (1H), 8.7~9.1 (4H), 9.9 (1H) |

EXAMPLE 6

The same procedures as described in Example 4 were repeated using 1 g of N-(2-aminopropyl)-5-isoquinolinesulfonamide obtained in Referential example 4, 0.56 g sodium hydroxide and 1.52 g of S-methylisothiourea sulfate to give 1.05 g of N-(2-guanidinopropyl)-5-isoquinolinesulfonamide, i.e., Compound (16) in a yield of 90%.

Mass spectrum (m/e): 308, 249, 207, 192 and 128.

NMR spectrum (D$_2$O, DCl,δ): 1.3~1.5 (3H), 3.0~3.3 (3H), 8.0~8.3 (1H), 8.7~9.1 (4H) and 9.9 (1H).

IR absorption spectrum ($\nu_{max}$, cm$^{-1}$): 3500, 3300, 1690, 1640, 1200, 1180 and 1030.

The same procedures as described above were repeated using the compounds of Formula (II) as set forth in Table 16 under the reaction conditions as set forth in

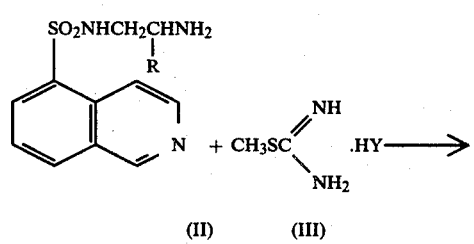

(II)      (III)

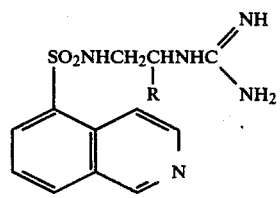

TABLE 16

| Run No. | R | (g) | (g) | Acid acceptor (g) | Solvent | Reaction Time (hour) | Reaction Temperature |
|---|---|---|---|---|---|---|---|
| 1 | i-Pr | 2.5 | CH₃SC(=NH)(NH₂)·½H₂SO₄ 3.42 | K₂CO₃ 2.12 | MeOH:H₂O 30:70 | 3 | Reflux |
| 2 | ph | 3.0 | CH₃SC(=NH)(NH₂)·HI 7.31 | NaOH 2.01 | H₂O | 4 | " |
| 3 | PhCH₂ | 2.5 | CH₃SC(=NH)(NH₂)·½H₂SO₄ 3.42 | NaOH 1.08 | Dioxan:H₂O 30:70 | 4 | " |

Structures above table: 
- Substrate: SO₂NHCH₂CHCHNH₂ (with R) on isoquinoline
- Reagent (III): CH₃SC(=NH)NH₂ · HY

TABLE 17

Product: SO₂NHCH₂CHNHC(=NH)NH₂ (with R) on isoquinoline

| Run No. | Compound No. | R | Yield [g] | (%) | Mass Spectrum (m/e) | IR Absorption Spectrum ($v_{max}$, cm⁻¹) | NMR Spectrum (D₂O, DCl, δ) |
|---|---|---|---|---|---|---|---|
| 1 | 19 | i-Pr | 2.29 | (80) | 336, 277, 235, 207, 192, 128 | 1690, 1640, 1200, 1170, 1040 | 1.0~1.2 (6H), 2.0~2.3 (1H), 3.0~3.3 (3H), 8.0~8.3 (1H), 8.7~9.1 (4H), 9.9 (1H) |
| 2 | 25 | Ph | 2.88 | (85) | 370, 311, 207, 192, 128 | 1700, 1640, 1200, 1170, 1040 | 3.0~3.4 (3H), 7.2 (5H), 8.0~8.3 (1H), 8.7~9.1 (4H), 9.9 (1H) |
| 3 | 26 | PhCH₂ | 2.27 | (81) | 384, 325, 207, 192, 128 | 1690, 1640, 1210, 1170, 1050 | 2.2~2.4 (2H), 3.0~3.3 (3H), 7.2 (5H), 8.0~8.3 (1H), 8.7~9.1 (4H), 9.9 (1H) |

EXAMPLE 7

The same procedure as described in Example 4 were repeated using 4.0 g of N-(4-amino-3-phenylbutyl)-5-isoquinolinesulfonamide obtained in Referential example 5, 4.29 g of S-methylisothiourea sulfate and 2.5 g of potassium carbonate to give 3.89 g of N-(4-guanidio-3-phenylbutyl)-5-isoquinolinesulfonamide, i.e., Compound (37) in a yield of 87%.

Mass spectrum (m/e): 398, 325, 207, 192 and 128.

NMR spectrum (D₂O, DCl,δ): 2.8~3.3 (5H), 1.7~1.9 (2H), 7.2 (5H), 8.0~8.3 (1H), 8.7~9.1 (4H) and 9.9 (1H).

IR absorption spectrum ($v_{max}$, cm⁻¹: 1700, 1640, 1180, 1160 and 1030.

The same procedures as described above were repeated using the compounds of Formua (II) as set forth in Table 18 under the reaction conditions as set forth in Table 18, and there were obtained N-(4-guanidino-3-methylbutyl)-5-isoquinolinesulfonamide, i.e., Compound (36), N-(5-guanidino-4-benzylpentyl)-5-isoquinolinesulfonamide, i.e., Compound (38), N-(5-guanidino-2-benzylpentyl)-5-isoquinolinesulfonamide, i.e., Compound (39) as set forth in Table 19.

The equation is as follows;

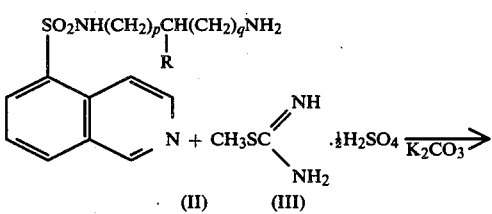

in Table 20-1 under the reaction conditions as set forth in Table 20-1, and there were obtained N-(6-guanidino-1-methylheptyl)-5-isoquinolinesulfonamide, i.e., Compound (43) as set forth in Table 20-2.

The equation is as follows:

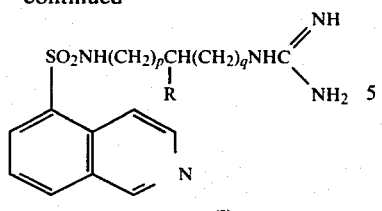

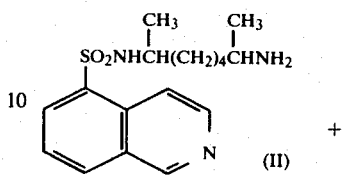

TABLE 18

| Run No. | p q | R | (II) (g) | Compound of Formula (III) (g) | K$_2$CO$_3$ (g) | Solvent | Reaction Temperature | Reaction Time (hour) |
|---|---|---|---|---|---|---|---|---|
| 1 | 2 1 | CH$_3$ | 2.5 | 3.79 | 2.4 | H$_2$O | 100° C. | 3 |
| 2 | 3 1 | PhCH$_2$ | 3.0 | 3.48 | 2.16 | EtOH:H$_2$O 70:30 | Reflux | 4 |
| 3 | 1 3 | PhCH$_2$ | 3.0 | 3.48 | 2.16 | EtOH:H$_2$O 70:30 | " | 4 |

TABLE 19

| Run No. | Compound No. | p q | R | Yield [g] | (%) | Mass Spectrum (m/e) | IR Absorption Spectrum ($\nu_{max}$, cm$^{-1}$) | NMR Spectrum (D$_2$O, DCl, δ) |
|---|---|---|---|---|---|---|---|---|
| 1 | 36 | 2 1 | CH$_3$ | 2.57 | (90) | 336 263, 207 192, 128 | 1680, 1620 1190, 1160 1030 | 1.0~1.2 (3H), 1.6~2.2 (3H), 3.0~3.3(4H), 8.0~8.3 (1H), 8.7~9.1 (4H), 9.9 (1H) |
| 2 | 38 | 3 1 | PhCH$_2$ | 2.93 | (88) | 426 353, 207 192, 128 | 1690, 1630 1200, 1170 1140 | 1.2~1.5 (2H), 1.6~2.0 (3H), 2.1~2.3 (2H), 3.0~3.3 (4H), 7.2 (5H), 8.0~8.3 (1H), 8.7~9.1 (4H), 9.9 (1H) |
| 3 | 39 | 1 3 | PhCH$_2$ | 2.96 | (89) | 426 325, 207 192, 128 | 1690, 1630 1340, 1170 1140 | 1.2~1.5 (2H), 1.6~2.3 (5H), 3.0~3.3 (4H), 7.2 (5H), 8.0~8.3 (1H), 8.7~9.1 (4H), 9.9 (1H) |

EXAMPLE 8

In 15 ml of water were suspended 3.0 g of N-(2-amino-1-methylpropyl)-5-isoquinolinesulfonamide obtained in Referential example 6, 4.48 g of S-methylisothiourea sulfate and 2.30 g of potassium carbonate, and the suspension was heated at reflux for two hours. The reaction mixture solution was cooled to 25° C., and the crystals precipitated were separated by filtration. The crystalline residue thus obtained was recrystallized from methanol to give 2.73 g of N-(2-guanidino-1-methylpropyl)-5-isoquinolinesulfonamide, i.e. Compound (41) in a yield of 79%.

Mass spectrum (m/e): 322, 263, 235, 207 and 128.

NMR spectrum (D$_2$O, DCl,δ): 1.1~1.4 (6H), 3.2~3.5 (2H), 8.0~8.3 (1H), 8.7~9.1 (4H) and 9.9 (1H).

IR absorption spectrum ($\nu_{max}$, cm$^{-1}$): 1680, 1640, 1200 and 1180.

The same procedures as described above were repeated using the compounds of Formula (II) as set forth

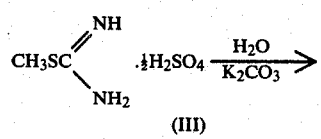

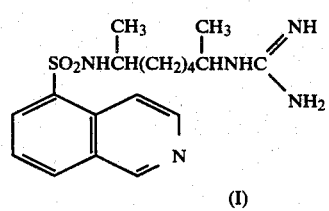

TABLE 20

| Compound of Formula (II) (g) | Compound of Formula (III) (g) | K₂CO₃ (g) | Reaction Temperature | Reaction Time (hour) |
|---|---|---|---|---|
| 3 | 3.8 | 2.01 | Reflux | 3 |

$$\text{SO}_2\text{NHCH(CH}_3\text{)(CH}_2\text{)}_4\text{CH(CH}_3\text{)NHC(=NH)NH}_2 \text{ - isoquinoline}$$

| Yield [g] | (%) | Mass Spectrum (m/e) | IR Absorption Spectrum ($v_{max}$, cm$^{-1}$) | NMR Spectrum (D₂O, DCl, δ) |
|---|---|---|---|---|
| 2.98 | (88) | 378, 319, 235, 207, 192, 128 | 3350, 3200, 1680, 1640, 1210, 1190 | 1.1~1.8 (14H), 3.1~3.5 (2H), 8.0~8.3 (1H), 8.7~9.1 (4H), 9.9 (1H) |

EXAMPLE 9

In 30 ml of water was dissolved 3.9 g of 1-amidinopiperazine sulfate, and 60 ml of tetrahydrofuran solution containing 4.1 g of 5-isoquinolinesulfonyl chloride and 1N sodium hydroxide was added dropwise under cooling with ice so that the pH of the solution maintain the range from 8 to 8.5. After the dropwise addition, the mixture solution was stirred for one hour. The crystalline residue was discarded, and the pH of the aqueous layer was adjusted to 1 with an aqueous diluted hydrochloric acid solution. The crystalline residue was discarded, and the pH of the aqueous layer was adjusted to 13 with a 5N aqueous sodium hydroxide solution. The crystals precipitated were separated by filtration, and the crystalline residue obtained was dissolved with an aqueous diluted hydrochloric acid solution. The pH of the solution was adjusted to 13.5 with a 2N aqueous sodium hydroxide solution. The crystals precipitated were separated by filtration, the crystalline residue was washed with water, methanol and ethylether and condensed to dryness to give 4.84 g of 4-amidino-1-(5-isoquinolinesulfonyl)piperazine, i.e., Compound (44) in a yield of 84%.

Mass spectrum (m/e): 319, 302, 278 and 221.

NMR spectrum (DMSO-d₆, D₂SO₄): 2.6~3.7 (8H), 7.7~8.3 (1H), 8.4~8.9 (4H) and 9.8 (1H).

IR spectrum ($v_{max}$, cm$^{-1}$): 3320, 1675, 1590 and 1170.

The same procedures as described above were repeated using the compounds of Formula (VIII) as set forth in Table 21 under the reaction conditions as set forth in Table 21, and there were obtained 4-amidino-1-(5-isoquinolinesulfonyl)homopiperazine, i.e., Compound (45), 4-amidino-1-(5-isoquinolinesulfonyl)-2-methylpiperazine, i.e., Compound (47) and 4-amidino-2,5-dimethyl-1-(5-isoquinolinesulfonyl)piperazine, i.e., Compound (49) as set forth in Table 22.

The equation is as follows;

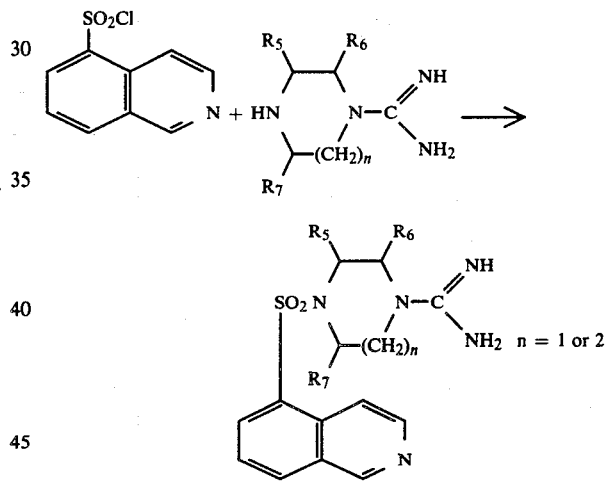

TABLE 21

| Run No. | (IV) (g) | n | R₅ R₆ R₇ | (g) | Reaction Temperature (°C.) | Reaction Time (hour) |
|---|---|---|---|---|---|---|
| 1 | 4.55 | 2 | H H H | 4.77 | 0~5 | 1 |
| 2 | 1.82 | 1 | CH₃ H H | 2.30 | " | " |
| 3 | 1.82 | 1 | H CH₃ CH₃ | 2.46 | " | " |

TABLE 22

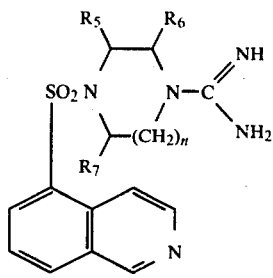

| Run No. | Compound No. | n | R5<br>R6<br>R7 | Yield [g] | (%) | Mass Spectrum (m/e) | IR Absorption Spectrum ($\nu_{max}$, cm$^{-1}$) | NMR Spectrum (D$_2$O, DCl, δ) |
|---|---|---|---|---|---|---|---|---|
| 1 | 45 | 2 | H<br>H<br>H | 4.80 | (72) | 333, 316<br>292, 221 | 3320, 1680<br>1590, 1160 | 1.5~1.9 (2H), 2.6~3.7 (8H), 7.5~8.3 (1H), 8.4~8.9 (4H), 9.8 (1H) |
| 2 | 47 | 1 | CH$_3$<br>H<br>H | 3.51 | (85) | 333, 316<br>292, 221 | 3330, 1680<br>1590, 1160 | 1.3 (3H), 2.4~3.6 (7H), 7.8~8.2 (1H), 8.3~8.9 (4H), 9.8 (1H) |
| 3 | 49 | 1 | H<br>CH$_3$<br>CH$_3$ | 2.19 | (79) | 347, 330<br>306, 221 | 3340, 1680<br>1590, 1160 | 0.8~1.4 (6H), 2.5~4.2 (6H), 7.8~8.3 (1H), 8.4~8.9 (4H), 9.8 (1H) |

EXAMPLE 10

In 10 ml of water were dissolved 1.00 g of N-(2-aminoethyl)-5-isoquinolinesulfonamide and 2.91 g of 2-methylthio-2-imidazoline hydrobromide, and to the mixture solution was added 0.83 g of potassium carbonate. After the solution was heated at reflux for three hours, the reaction mixture solution was cooled to 25° C., and the crystals precipitated were separated by filtration. The crystalline residue thus obtained was recrystallized from ethanol to give 0.95 g of 2-[2-(5-isoquinolinesulfonamide)ethylamino]-2-imidazoline in a yield of 75%.

Mass spectrum (m/e): 319, 235, 207, 192 and 128.

NMR spectrum (DCl, D$_2$O, δ): 3.0~3.5 (4H), 3.9 (4H), 8.0~8.3 (1H), 8.7~9.1 (4H) and 9.9 (1H).

IR absorption spectrum ($\nu_{max}$, cm$^{-1}$): 3500, 3300, 1700, 1630, 1340, 1170 and 1140.

The same procedures as described above were repeated using the compounds of Formula (III) as set forth in Table 23 under the reaction conditions as set forth in Table 23, and there were obtained 2-[2-(5-isoquinolinesulfonamido)ethylamino]-1,4,5,6-tetrahydropropyrimidine, i.e., Compound (51), N-[2-2,3-dimethylguanidio)ethyl]-5-isoquinolinesulfonamide, i.e., Compound (53), N-[2-(2,3-diethylguanidino)ethyl]-5-isoquinolinesulfonamide, i.e., Compound (54), N-[2-(3-methylguanidino)ethyl]-5-isoquinolinesulfonamide, i.e., Compound (52) and N-[2-(3-ethylguanidino)ethyl]-5-isoquinolinesulfonamide, i.e., Compound (55) as set forth in Table 24.

The equation is as follows;

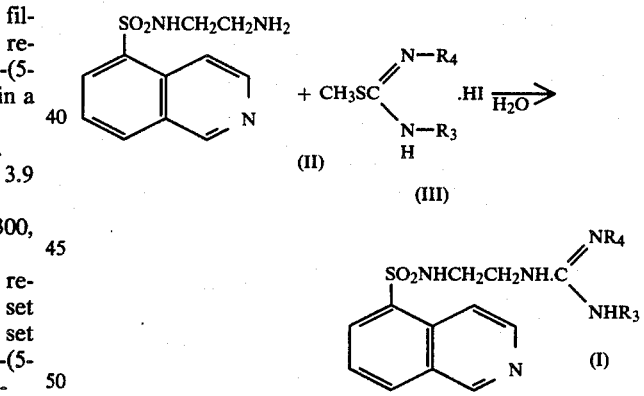

TABLE 23

| Run No. | (II) (g) | R$_3$ | R$_4$ | (III) (g) | K$_2$CO$_3$ (g) | Reaction Temperature | Reaction Time (hour) |
|---|---|---|---|---|---|---|---|
| 1 | 1 | —CH$_2$CH$_2$CH$_2$— | | 3.08 | 0.85 | Reflux | 3 |
| 2 | " | CH$_3$ | CH$_3$ | 2.94 | " | " | " |
| 3 | " | C$_2$H$_5$ | C$_2$H$_5$ | 3.27 | " | " | " |
| 4 | " | H— | CH$_3$— | 2.77 | " | " | " |
| 5 | " | H | C$_2$H$_5$ | 2.94 | " | " | " |

TABLE 24

SO$_2$NHCH$_2$CH$_2$NH.C(=NR$_4$)NHR$_3$ on isoquinoline (I)

| Run No. | Compound No. | R$_3$ | R$_4$ | Yield [g] | (%) | Mass Spectrum (m/e) | IR Absorption Spectrum ($\nu$max, cm$^{-1}$) | NMR Spectrum (D$_2$O,DCl,$\delta$) |
|---|---|---|---|---|---|---|---|---|
| 1 | 51 | —CH$_2$CH$_2$CH$_2$— | | 1.02 | (77) | 334, 235, 207, 192, 128 | 1700, 1620, 1340, 1170, 1140 | 1.5~1.7 (2H), 3.0~3.3 (8H), 8.7~9.1 (4H), 9.9 (1H), 8.0~8.3 (1H) |
| 2 | 53 | CH$_3$ | CH$_3$ | 1.09 | (85) | 322, 235, 207, 192, 128 | 1700, 1630, 1340, 1160, 1130 | 3.0~3.3 (10H), 8.7~9.1 (4H), 9.9 (1H), 8.0~8.3 (1H) |
| 3 | 54 | C$_2$H$_5$ | C$_2$H$_5$ | 1.25 | (90) | 350, 235, 207, 192, 128 | 1690, 1630, 1350, 1150, 1120 | 1.4 (6H), 3.0~3.3 (8H), 8.0~8.3 (1H), 8.7~9.1 (4H), 9.9 (1H) |
| 4 | 52 | H | CH$_3$ | 0.966 | (79) | 308, 235, 207, 192, 128 | 1680, 1640, 1350, 1150, 1120 | 3.0~3.3 (7H), 8.0~8.3 (1H), 8.7~9.1 (4H), 9.9 (1H) |
| 5 | 55 | H | C$_2$H$_5$ | 1.09 | (85) | 322, 235, 207, 192, 128 | 1680, 1630, 1350, 1160, 1140 | 1.4 (3H), 3.0~3.3 (6H), 8.0~8.3 (1H), 8.7~9.1 (4H), 9.9 (1H) |

EXAMPLE 11

In 20 ml of methanol was suspended 1.0 g of N-(2-guanidinoethyl)-5-isoquinolinesulfonamide, i.e., Compound (2), the crystalline residue was dissolved with 7.5 ml of 1N aqueous hydrochloride solution. The reaction mixture solution was condensed to dryness under reduced pressure, the crystalline residue thus obtained was recrystallized from methanol to give 1.12 g of N-(2-guanidinoethyl)-5-isoquinolinesulfonamide dihydrochloride in a yield of 90%.

Elemental Analysis Value: Calcd. (%): C 39.35; H 4.68; N 19.12; S 8.75; Cl 19.36. Found (%): C 39.4; H 4.8; N 19.0; S 8.7; Cl 19.4.

The same procedures as described above were repeated using the compounds of Formula (I) as set forth in Table 25 under the reaction conditions as set forth in Table 25, and there were obtained dihydrochloric acid salts of the compounds of Formula (I) as set forth in Table 25.

The equation is as follows;

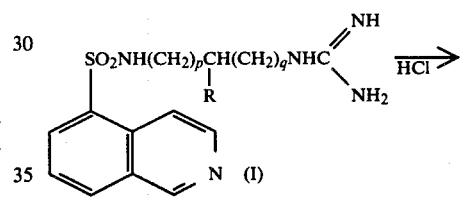

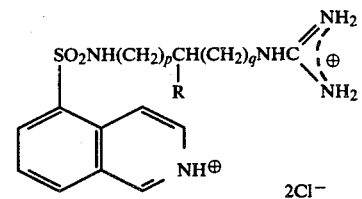

TABLE 25

SO$_2$NH(CH$_2$)$_p$CH(CH$_2$)$_q$NHC(=NH$_2^\oplus$)NH$_2$ with R substituent on isoquinoline·NH$^\oplus$ 2Cl$^-$

| Run No. | Compound of Formula (I) (g) | Compound No. | p q | R | [g] | (%) | Calcd. (%) | Found (%) |
|---|---|---|---|---|---|---|---|---|
| 1 | 1 | 3 | 0 2 | H | 1.11 | (90) | C 41.06; H 5.04; N 18.42 Cl 18.65; S 8.43 | C 41.2; H 5.1; N 18.3 Cl 18.5; S 8.4 |
| 2 | " | 4 | 0 3 | " | 1.09 | (89) | C 42.65; H 5.37; N 17.76 Cl 17.98; S 8.13 | C 42.5; H 5.4; N 17.7 Cl 17.8; S 8.0 |
| 3 | " | 5 | 0 4 | " | 1.11 | (91) | C 44.12; H 5.68, N 17.15 Cl 17.36; S 7.85 | C 44.0; H 5.7; N 17.2 Cl 17.3; S — |
| 4 | " | 6 | 0 5 | " | 1.03 | (85) | C 45.50; H 5.97; N 16.58 Cl 16.79; S 7.59 | C —; H —; N — Cl —; S — |
| 5 | " | 7 | 0 7 | " | 1.06 | (89) | C 48.00; H 6.49, N 15.55 Cl 15.74; S 7.12 | C 47.9; H 6.5; N 15.4 Cl 15.8; S — |
| 6 | " | 8 | 0 9 | " | 1.03 | (87) | C 50.42; H 6.56; N 14.70 Cl 14.88; S 6.73 | C 50.6; H 6.6; N 14.7 Cl 14.9; S 6.7 |
| 7 | " | 9 | 0 1 | CH$_3$ | 1.13 | (91) | C 41.06; H 5.04; N 18.42 Cl 18.65; S 8.43 | C 41.1; H 5.1; N 18.5 Cl 18.8; S — |

TABLE 25-continued

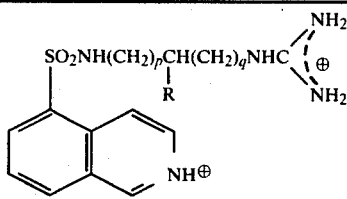

2Cl⁻

| Run No. | Compound of Formula (I) (g) | Compound No. | p / q | R | [g | (%)] | Calcd. (%) | Found (%) |
|---|---|---|---|---|---|---|---|---|
| 8 | " | 10 | 0 / 1 | $C_2H_5$ | 1.10 | (90) | C 42.65; H 5.37; N 17.76 Cl 17.98; S 8.13 | C 42.7; H 5.5; N 17.8 Cl 18.0; S — |
| 9 | " | 13 | 0 / 1 | n-$C_4H_9$ | 1.06 | (88) | C 45.50; H 5.97; N 16.58 Cl 16.79; S 7.59 | C 45.6; H 5.9; N 16.5 Cl 16.8; S — |
| 10 | " | 16 | 1 / 0 | $CH_3$ | 1.11 | (90) | C 41.06; H 5.09; N 18.42 Cl 18.65; S 8.43 | C 41.0; H 5.1; N 18.4 Cl 18.7; S 8.5 |
| 11 | " | 17 | 1 / 0 | $C_2H_5$ | 1.12 | (91) | C 42.65; H 5.37; N 17.76 Cl 17.98; S 8.13 | C —; H —; N — Cl —; S — |
| 12 | " | 19 | 1 / 0 | i-$C_3H_7$ | 1.05 | (86) | C 44.12; H 5.68; N 17.15 Cl 17.36; S 7.85 | C 44.0; H 5.7; N 17.1 Cl 17.3; S — |
| 13 | " | 23 | 0 / 1 | Ph | 1.05 | (88) | C 48.87; H 4.79; N 15.83 Cl 16.03; D 7.25 | C 48.8; H 4.7; N 15.8 Cl 15.9; S — |
| 14 | " | 24 | 0 / 1 | $PhCH_2$ | 1.04 | (87) | C 50.00; H 5.08; N 15.34 Cl 15.54; S 7.02 | C 50.0; H 5.2; N 15.4 Cl 15.5; S — |
| 15 | " | 25 | 1 / 0 | Ph | 1.09 | (91) | C 48.87; H 4.79; N 15.83 Cl 16.03; S 7.25 | C 48.9; H 4.7; N 15.7 Cl 16.0; S — |
| 16 | " | 35 | 2 / 0 | $PhCH_2$ | 1.01 | (85) | C 50.00; H 5.08; N 15.34 Cl 15.54; S 7.02 | C 49.9; H 5.1; N 15.3 Cl 15.4; S — |
| 17 | " | 28 | 1 / 1 | $CH_3$ | 1.09 | (89) | C 42.65; H 5.37; N 17.76 Cl 17.98; S 8.13 | C 42.8; H 5.4; N 17.8 Cl 18.0; S — |
| 18 | " | 31 | 1 / 1 | Ph | 1.01 | (85) | C 50.00; H 5.08; N 15.34 Cl 15.54; S 7.02 | C 49.9; H 5.0; N 15.5 Cl 15.6; S — |
| 19 | " | 34 | 1 / 1 | $PhCH_2$ | 1.03 | (87) | C 51.07; H 5.36; N 14.89 Cl 15.07; S 6.82 | C 51.1; H 5.4; N 14.8 Cl 15.1; S — |
| 20 | " | 36 | 2 / 1 | $CH_3$ | 1.07 | (88) | C 44.12; H 5.68; N 17.15 Cl 17.36; S 7.85 | C 44.0; H 5.6; N 17.1 Cl 17.4; S — |
| 21 | " | 37 | 2 / 1 | Ph | 1.07 | (90) | C 51.07; H 5.36; N 14.89 Cl 15.07; S 6.82 | C 51.0; H 5.4; N 14.9 Cl 15.0; S — |
| 22 | " | 38 | 3 / 1 | $PhCH_2$ | 1.07 | (91) | C 53.01; H 5.86; N 14.05 Cl 14.22; S 6.43 | C 53.3; H 5.9; N 14.0 Cl 14.1; S — |
| 23 | " | 39 | 1 / 3 | $PhCH_2$ | 1.07 | (91) | C 53.01; H 5.86; N 14.05 Cl 14.22; S 6.43 | C 53.1; H 5.9; N 14.1 Cl 14.2; S — |

EXAMPLE 12

50 ml of methanol was suspended 20.5 g of N-(2-guanidinoethyl)-5-isoquinolinesulfonamide, and the mixture solution was dissolved completely with 30 ml of methanol solution containing 13.32 g of p-toluenesulfonic acid hydrate. The methanol was distilled therefrom under reduced pressure, the crystalline residue was recrystallized from water to give 24.8 g of N-(2-guanidinoethyl)-5-isoquinoline-sulfonamide-p-toluenesulfonate in a yield of 76.1%. The melting point of the compound was the range from 148° C. to 149° C.

EXAMPLE 13

In 55 ml of water was suspended 20.5 g of N-(2-guanidinoethyl)-5-isoquinolinesulfonamide, the crystalline residue was dissolved by slowly adding of 8.2 ml of an aqueous concentrated hydrochloric acid solution. The pH of the aqueous layer was adjusted to 6.8 with 3.2 ml of a 10N aqueous sodium hydroxide solution by dropwise addition at a temperature of 30° C. to 40° C., and the mixed solution was stirred for a night. The crystalline residue thus obtained was separated by filtration, and the residue was recrystallized from 50 ml of water to give 18.9 g of N-(2-guanidinoethyl)-5-isoquinolinesulfonamide monohydrochloride in a yield of 82%. The melting point of the compound was 236° C.

Elemental Analysis Value: Calcd. (%): C 43.70; H 4.89; N 21.23; Cl 10.75. Found (%): C 44.01; H 5.00; N 20.95; Cl 10.92.

RELAXATION OF MESENTERIC ARTERY

After a home bred rabbit of a Japanese species weighing about 3 Kg was subjected to bloodletting, resulting in death and then to abdominal incision, the mesenteric artery was taken out, cut into helicoids of 2 mm×25 mm and suspended in a 20 ml organ bath filled with a Krebs-Henseleit solution into which a mixed gas of 95% by volume of $O_2$ and 5% by volume of $CO_2$ was introduced and one end of the artery was connected with an isometric transducer. When a load of 1.5 g was applied to the artery, the contraction and the relaxation of the artery were recorded as a weight on the transducer (a product of Nippon Koden K.K., Japan, "FD Pickup TB-912T"). The relaxation of the mesenteric artery was observed by adding the isoquinolinesulfonamide derivatives and their pharmaceutically acceptable acid addition salts of this invention to the mesenteric artery at the condition of about one half of the maximum contraction with KCl concentration of 15-20 mM. When the complete relaxation of the mesenteric artery was designated 100%, the concentration of the isoquinolinesulfonamide derivatives and their pharmaceutically acceptable acid addition salts which brought about a relaxation of 50% is shown in Table 26.

TABLE 26

| Compound Nos. | Relaxation of Mesenteric Artery ED$_{50}$ ($\mu$M) | Compound Nos. | Relaxation of Mesenteric Artery ED$_{50}$ ($\mu$M) |
| --- | --- | --- | --- |
| 2 | 1 | 6 | 4 |
| 3 | 2 | 7 | 10 |
| 4 | 2 | 8 | 15 |
| 5 | 3 | 9 | 3 |
| 10 | 5 | 39 | 13 |
| 13 | 13 | 50 | 20 |
| 16 | 3 | 51 | 25 |
| 17 | 10 | 52 | 7 |
| 19 | 15 | 53 | 10 |
| 23 | 8 | 54 | 12 |
| 24 | 10 | 55 | 5 |
| 25 | 10 | 41 | 8 |
| 28 | 3 | 43 | 5 |
| 31 | 2 | 44 | 0.6 |
| 34 | 2 | 45 | 2 |
| 35 | 5 | 49 | 1 |
| 36 | 5 | | |
| 37 | 10 | | |
| 38 | 11 | | |

EFFECT ON BLOOD FLOW VOLUME OF FEMORAL AND VERTEBRAL ARTERIES OF DOGS, AND AN HYPOTENSIVE ACTION

The effect on the vasodilatation of the femoral and vertebral arteries was measured by anesthetizing a dog of mixed breed weighing 8 to 15 Kg by an intravenous administration of 35 mg/Kg of pentbarbitol, providing an acute type probe (a product of Nippon Koden K.K., Japan) with the femoral and vertebral arteries, administering to the femoral vein through a polyethylene tube inserted into the femoral vein side chain, measuring the blood flow volume with an electromagnetic blood flowmeter (a product of Nippon Koden K.K., Japan, "MFV-1200") and measuring the change of blood pressure. The results are shown in Table 27.

TABLE 27

| Compound Nos. | Amount of Intravenous Administration (mm/Kg) | Increased Blood Flow Volume in Femoral Artery (%) | Increased Blood Flow Volume in Vertebral Artery (%) | Average Decreased Blood Pressure (mmHg) | Duration Time (Min.) |
| --- | --- | --- | --- | --- | --- |
| 2 | 1 | 37 | 95 | 32 | >30 |
| 31 | 1 | 30 | 75 | 15 | 28 |
| 43 | 1 | 32 | 68 | 15 | 25 |
| 44 | 0.5 | 29 | 60 | 50 | >30 |
| 50 | 1 | 19 | 65 | 10 | 21 |

ACUTE TOXICITY

The acute toxicity of the N-(2-guanidinoethyl)-5-isoquinolinesulfonamide dihydrochloride was measured by giving male ddY-strain mouse and rat an intravenous administration and an oral administration. The results are shown in Table 28.

TABLE 28

| LD$_{50}$ (mg/Kg) | | | |
| --- | --- | --- | --- |
| Intravenous administration | | Oral administration | |
| δ mouse | δ rat | δ mouse | δ rat |
| 59 | 64 | 1480 | 1156 |

The acute toxicity of the hydrochloride acid salt of other compounds was measured by giving male ddY-strain mice an intravenous administration. The results are shown in Table 29.

TABLE 29

| Compound Nos. | LD$_{50}$ (mg/Kg) |
| --- | --- |
| 31 | 80 |
| 43 | 66 |
| 44 | 12 |

What is claimed is:

1. A compound of Formula (I):

$$\text{SO}_2-\underset{R_1}{\overset{|}{N}}-A-\underset{R_2}{\overset{|}{N}}C\overset{NR_4}{\underset{NHR_3}{\diagup\!\!\!\diagdown}}$$

wherein A is a single bond; a $C_{1-10}$ alkylene group; or a $C_{1-10}$ alkylene group having one or two groups selected from the groups consisting of $C_{1-10}$ alkyl group, a phenyl group or a phenylalkyl having a $C_{1-2}$ alkyl portion;

$R_1$ and $R_2$ each is a hydrogen atom;

$R_3$ and $R_4$ each is a hydrogen atom or a $C_{1-6}$ alkyl group; or a pharmaceutically acceptable acid addition salt thereof.

2. The compound of claim 1 wherein A is an unsubstituted $C_{1-10}$ alkylene group; and $R_3$ and $R_4$ each is a hydrogen atom.

3. The compound of claim 2 wherein A is an ethylene group.

4. The compound of claim 1 wherein A is a unsubstituted ethylene group; at least one of $R_3$ and $R_4$ is a $C_{1-6}$ alkyl group.

5. The compound of claim 4 wherein one of $R_3$ and $R_4$ is a hydrogen atom, a methyl group or a ethyl group, the other of $R_3$ and $R_4$ is a methyl group or an ethyl group.

6. The compound according to claim 1 wherein A is a $C_{1-10}$ alkylene group having a $C_{1-10}$ alkyl group, a phenyl group or a phenylalkyl having a $C_{1-2}$ alkyl portion.

7. The compound according to claim 6, wherein $R_1$, $R_2$, $R_3$ and $R_4$ each is a hydrogen atom.

8. The compound according to claim 1, wherein A is a $C_{2-6}$ alkylene group having one or two $C_{1-4}$ alkyl groups.

9. A compound of Formula (I):

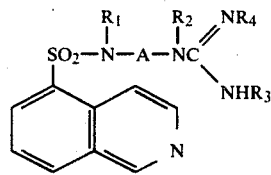

wherein A is a $C_{2-6}$ alkylene group having one or two groups selected form the group consisting of $C_{1-10}$ alkyl group, a phenyl group and a phenylalkyl group having a $C_{1-2}$ alkyl portion;

$R_1$ and $R_2$ each is a hydrogen atom;

$R_3$ and $R_4$ each is a hydrogen atom, a $C_{1-6}$ alkyl group; or a pharmaceutically acceptable acid addition salt thereof.

10. The compound of claim 8 wherein A is a $C_{2-6}$ alkylene group having a $C_{1-4}$ alkyl group.

11. The compound of claim 8 wherein A is a $C_{2-6}$ alkylene group having one phenyl group or one benzyl group.

* * * * *